United States Patent
Kitahara et al.

(10) Patent No.: US 7,002,009 B2
(45) Date of Patent: Feb. 21, 2006

(54) CRYSTALLINE TRICYCLIC TRIAZOLOBENZAZEPINE DERIVATIVE

(75) Inventors: Shin-Ichi Kitahara, Kanagawa-Ken (JP); Hanae Furukawa, Kanagawa-Ken (JP); Toshihiro Yamaguchi, Kanagawa-Ken (JP); Sachiko Miyamoto, Kanagawa-Ken (JP); Yumiko Okada, Kanagawa-Ken (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 23 days.

(21) Appl. No.: 10/500,157

(22) PCT Filed: Dec. 25, 2002

(86) PCT No.: PCT/JP02/13557

§ 371 (c)(1),
(2), (4) Date: Jun. 25, 2004

(87) PCT Pub. No.: WO03/055885

PCT Pub. Date: Jul. 10, 2003

(65) Prior Publication Data

US 2005/0020579 A1    Jan. 27, 2005

(30) Foreign Application Priority Data

Dec. 26, 2001 (JP) .............. 2001-393016

(51) Int. Cl.
*C07D 487/04* (2006.01)
(52) U.S. Cl. ..................................... 540/521
(58) Field of Classification Search ........... 540/521; 514/212.06
See application file for complete search history.

(56) References Cited

U.S. PATENT DOCUMENTS 6,372,735 B1 * 4/2002 Ohtsuka et al. ......... 514/212.06

FOREIGN PATENT DOCUMENTS

WO    WO 97/32883  A1    9/1997
WO    WO 99/16770  A1    4/1999

* cited by examiner

*Primary Examiner*—Bruck Kifle
(74) *Attorney, Agent, or Firm*—Heller Ehrman LLP

(57) ABSTRACT

Disclosed are novel crystalline 2-(1-isopropoxycarbonyloxy-2-methylpropyl)-7,8-dimethoxy-4(5H),10-dioxo-2H-1,2,3-triazolo[4,5-c][1]benzazepine and a pharmaceutical composition comprising the same.

3 Claims, 2 Drawing Sheets

CRYSTALLINE TRICYCLIC TRIAZOLOBENZAZEPINE DERIVATIVE

BACKGROUND OF THE INVENTION

1. Field of the Invention

The present invention relates to a novel crystalline 2-(1-isopropoxycarbonyloxy-2-methylpropyl)-7,8-dimethoxy-4(5H),10-dioxo-2H-1,2,3-triazolo[4,5-c][1]benzazepine which is useful as medicaments.

2. Background Art 2-(1-Isopropoxycarbonyloxy-2-methylpropyl)-7,8-dimethoxy-4(5H),10-dioxo-2H-1,2,3-triazolo[4,5-c][1]benzazepine (hereinafter referred to as "compound A") is a compound, represented by the following chemical structural formula, which is expected to be utilized as an antiallergic agent, as described in WO 99/16770 (Japanese Patent No. 3188482 and U.S. Pat. No. 6,372,735) (the disclosure of each of these publications is incorporated herein by reference).

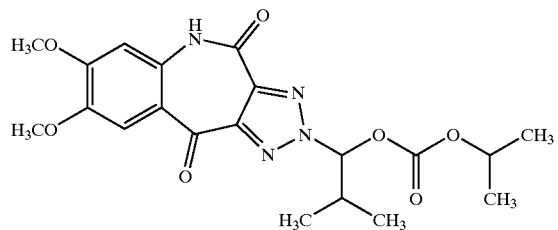

The product obtained by the method described in the above publications, is a light yellow powder which is low in compound A purity as determined based on percentage area obtained by HPLC analysis. The product is estimated to be a mixture of compound A with its decomposition product(s) and analogs and the like.

In the production of medicaments, constantly providing a compound having an identical quality is necessary for constantly providing given activity and effect. Therefore, in order to ensure the even quality which is required in a starting material for the production of medicaments as well as the given activity and effect thereof, a pure compound should be constantly produced. Furthermore, stable crystals, which can maintain the same quality, are also desired from the viewpoint of good storage stability.

SUMMARY OF THE INVENTION

The present inventors have now succeeded in providing a novel high-purity and stable crystalline compound A. Further, the present inventors have found a production process which can stably supply a large amount of a novel high-purity crystalline compound A with high efficiency. The present invention has been made based on such finding.

Accordingly, an object of the present invention is to provide a crystalline compound A and a process for producing the same.

Crystalline compound A according to the present invention exhibits large diffraction peaks at diffraction angles (2θ): 11.2±0.1°, 14.4±0.1°, 15.5±0.1°, and 25.3±0.1° in a powder X-ray diffraction pattern.

DETAILED DESCRIPTION OF THE INVENTION

Figure 1:
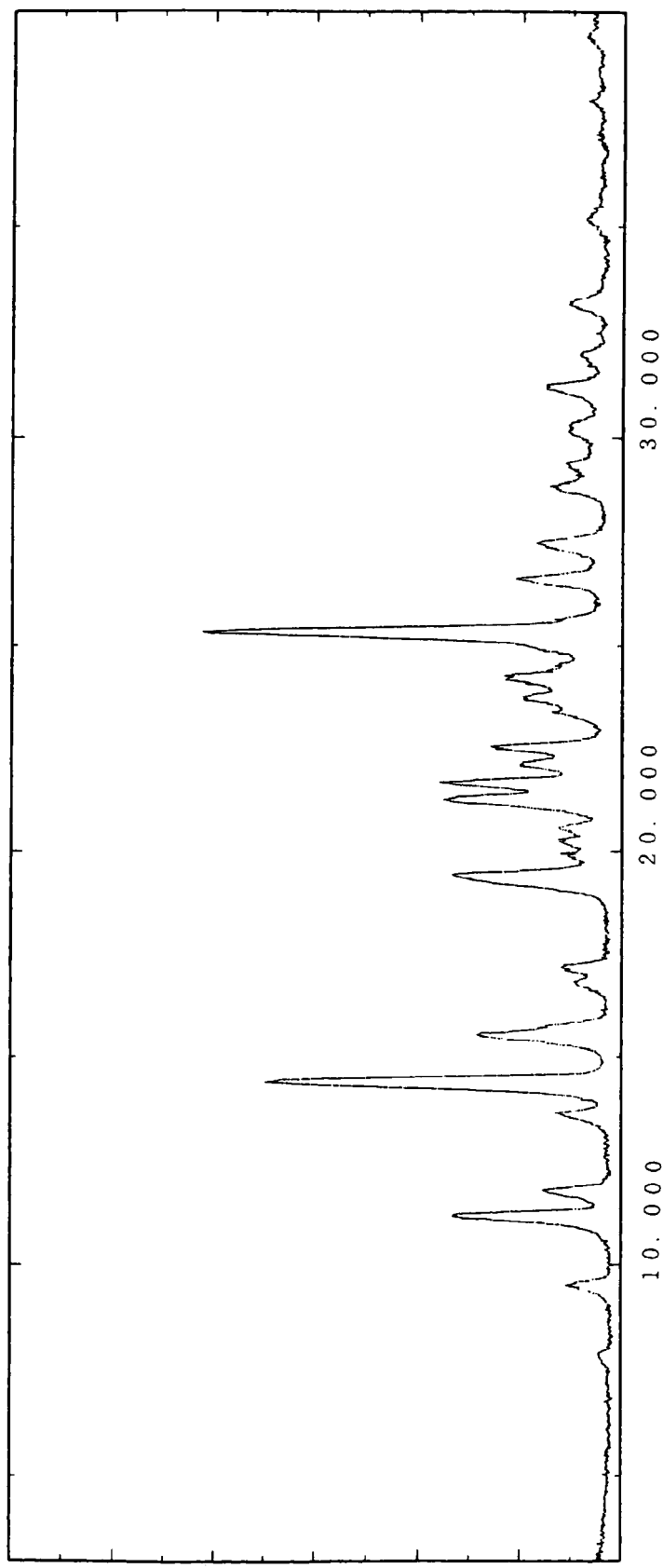
FIG. 1 is a powder X-ray diffraction pattern of a crystalline compound produced in Example 1.

Crystalline compound A according to the present invention exhibits large diffraction peaks at diffraction angles (2θ): 11.2±0.1°, 14.4±0.1°, 15.5±0.1°, and 25.3±0.1° in a powder X-ray diffraction pattern. Further, the crystalline compound A has a melting point in the temperature range of 240 to 246° C. (with decomposition) as determined from an endothermic peak in a chart obtained by differential scanning calorimetry (DSC). The crystalline compound A according to the present invention is of a stable form. Since the compound A product having specific physicochemical properties thus identified has not hitherto been known at all, it is novel crystalline substance of compound A. Further, the crystalline substance according to the present invention has a purity of not less than 99% for compound A as determined based on percentage area obtained by HPLC (high-performance liquid chromatography). Therefore, the novel crystalline compound A according to the present invention has high purity and can be advantageously used as bulk powder of medicaments. Specifically, the crystalline compound A according to the present invention can be used in the prophylaxis or therapy of allergic diseases. Allergic diseases include, for example, bronchial asthma, eczema, hives, allergic gastrointestinal injury, allergic rhinitis, and allergic conjunctivitis. Accordingly, in another aspect of the present invention, there is provided a composition, especially a pharmaceutical composition, comprising the crystalline compound A according to the present invention. Further, in still another aspect of the present invention, there is provided a method for preventing or treating an allergic disease, said method comprising the step of administering the crystalline compound A according to the present invention to an animal including a human. Furthermore, in a further aspect of the present invention, there is provided use of the crystalline compound A according to the present invention, for the production of an antiallergic agent.

The crystalline compound A according to the present invention can be preferably produced by the following production processes.

The first production process is as follows. In the first production process, basically, compound A is suspended or dissolved in methylene chloride to prepare a suspension or a solution, and powder is obtained from the suspension or the solution and is subjected to crystallization at least once from 2-propanol. More specifically, methylene chloride is added to compound A. The mixture is stirred to prepare a suspension, and the solvent is removed by evaporation using a rotary evaporator. 2-Propanol is added to the residue to prepare a suspension which is then stirred for 1 to 5 hr. After the suspension is filtered, 2-propanol is again added to prepare a suspension which is then stirred for 1 to 5 hr. Further, after the suspension is filtered again, and a 10% aqueous 2-propanol solution is then added to the collected sample to prepare a suspension which is then stirred for 1 to 2 days. After filtration, the collected sample is dried in vacuo at room temperature to give the crystalline compound A according to the present invention.

The second production process is as follows. In the second production process, basically, ethyl 5-(2-amino-4,5-dimethoxybenzoyl)-2-(1-isopropoxycarbonyloxy-2-methylpropyl)-2H-1,2,3-triazole-4-carboxylate is reacted with acetic acid to give a mixture containing compound A, methylene chloride is added to this mixture, the mixture is washed with water, an aqueous sodium bicarbonate solution, and brine, the organic layer is concentrated, and methylene chloride in the concentrate is then replaced by methanol for crystallization. More specifically, ethyl 5-(2-amino-4,5-dimethoxybenzoyl)-2-(1-isopropoxycarbonyloxy-2-methylpropyl)-2H-1,2,3-triazole-4-carboxylate (which can be produced by the method described in Example 20b of WO 99/16770) is suspended in acetic acid to prepare a suspension. The suspension is stirred at 10 to 40° C. (preferably 20 to 30° C.) for 15 to 18 hr and then at 90 to 110° C. (preferably 95 to 105° C.) for 4 to 6 hr. After the completion of the reaction, methylene chloride is added to the reaction solution. The mixed solution is washed with water, a 5 to 8% aqueous sodium bicarbonate solution, and further 20% brine. After the organic layer is dehydrated over anhydrous sodium sulfate or anhydrous magnesium sulfate, the dehydrated organic layer is concentrated under the reduced pressure. Methanol is added to the concentrate, and the mixture is again concentrated. The above procedure is repeated once more, followed by stirring at 0 (zero) to 10° C. (preferably 3 to 7° C.) for 10 to 20 hr (preferably 15 to 18 hr) for crystallization. The crystal is collected by filtration, is washed with methanol cooled at 0 (zero) to 10° C., and is then dried in vacuo at 40 to 50° C. to give the crystalline compound A according to the present invention. The amounts of acetic acid used in this reaction and other materials are preferably the following amounts per g of ethyl 5-(2-amino-4,5-dimethoxybenzoyl)-2-(1-isopropoxycarbonyloxy-2-methylpropyl)-2H-1,2,3-triazole-4-carboxylate. Specifically, the amount of acetic acid is preferably 3 to 10 mL. The amount of methylene chloride added after the completion of the reaction is preferably 10 to 20 mL. The amount of water used in washing the organic layer is preferably 10 to 20 mL. The amount of the 5 to 8% aqueous sodium bicarbonate solution is preferably 5 to 10 mL. The amount of brine is preferably 10 to 20 mL. In the concentration in vacuo after the dehydration, the solution is preferably concentrated to a volume of 3 to 5 mL. The amount of methanol added after the concentration is preferably 5 to 20 mL. After the addition of methanol, the solution is preferably concentrated in vacuo to a volume of 3 to 10 mL. This second production process is especially suitable for the supply of a large amount of the crystalline compound A.

EXAMPLES

The present invention is further illustrated by the following Examples that are not intended as a limitation of the invention.

Example 1

Production Process 1 of Compound A

Methylene chloride (0.2 L) was added to 10.01 g of compound A produced in the method described in Example 20 of WO 99/16770, and the mixture was stirred to prepare a suspension. The solvent was removed by evaporation using a rotary evaporator. 2-Propanol (0.2 L) was added to the residue to prepare a suspension which was then stirred for 3 hr. After the suspension was filtered, 0.2 L of 2-propanol was again added to the collected sample to prepare a suspension which was then stirred for 3 hr. The stirred suspension was further filtered, and 0.2 L of a 10% aqueous 2-propanol solution was then added to the collected sample to prepare a suspension which was then stirred for one day. After the filtration, the collected sample was dried at room temperature in vacuo for about 18 hr to give a crystalline substance of compound A (9.79 g, yield 97.8%).

Example 2

Production Process 2 of Compound A

Ethyl 5-(2-amino-4,5-dimethoxybenzoyl)-2-(1-isopropoxy-carbonyloxy-2-methylpropyl)-2H-1,2,3-triazole-4-carboxylate (6 kg) was suspended in 60 L of acetic acid, and the suspension was then stirred at 17 to 30° C. for 15 hr and then 92 to 97° C. for 4.5 hr. After methylene chloride (120 L) was added to the reaction solution, the mixture was washed twice with 120 L of water, twice with 60 L of a 7% aqueous sodium bicarbonate solution, and further with 120 L of 20% brine. The organic layer was dehydrated over 2 kg of anhydrous sodium sulfate, and the dehydrated organic layer was then concentrated to a volume of 30 L under the reduced pressure. After methanol (60 L) was added to the concentrated solution, the solution was again concentrated to a volume of 30 L under the reduced pressure. The above procedure was repeated, and the concentrated solution was stirred at 5° C. for 18 hr. The precipitated crystal was collected by filtration, was washed with methanol cooled at 3° C., and was then dried at 40° C. under the reduced pressure to give a crystalline substance of compound A (5.08 kg, yield 93.7%).

Evaluation Example 1

Powder X-ray Diffraction

The crystalline substance produced in Example 1 was evaluated by a powder X-ray diffraction device. Measuring conditions for the evaluation were as follows.

Apparatus: RINT 2100 (manufactured by Rigaku Corporation)

Measuring conditions: X ray: CuKα$_1$; tube voltage: 40 kV; tube current: 20 mA; monochromatization: graphite monochromator; scanning speed: 4°/min; scanning step: 0.02°; scanning axis: 2θ/θ; divergent slit: 1°; scattering slit: 1°; light receiving slit: 0.3 mm; scanning range: 2θ=3 to 40°

A powder X-ray diffraction pattern of the crystalline substance according to the present invention produced in Example 1 is shown in FIG. 1.

In the powder X-ray diffraction pattern of the crystalline substance produced in Example 1, characteristic peaks were observed at diffraction angles (2θ) of 11.2±0.1°, 14.4±0.1°, 15.5±0.1°, and 25.3±0.1°, indicating that the substance is crystalline.

Evaluation Example 2

DSC

The crystalline substance produced in Example 1 was evaluated with a differential scanning calorimeter. Measuring conditions for the evaluation were as follows.

Apparatus: DSC 220 U (manufactured by Seiko Instruments Inc.)

Measuring conditions: Open aluminum pan was packed with sample (3 to 5 mg), and the measurement was carried out in a nitrogen atmosphere (gas flow rate 20 mL/min) at a heating rise rate of 5° C./min in the measuring temperature range of 50 to 280° C.

Figure 2:
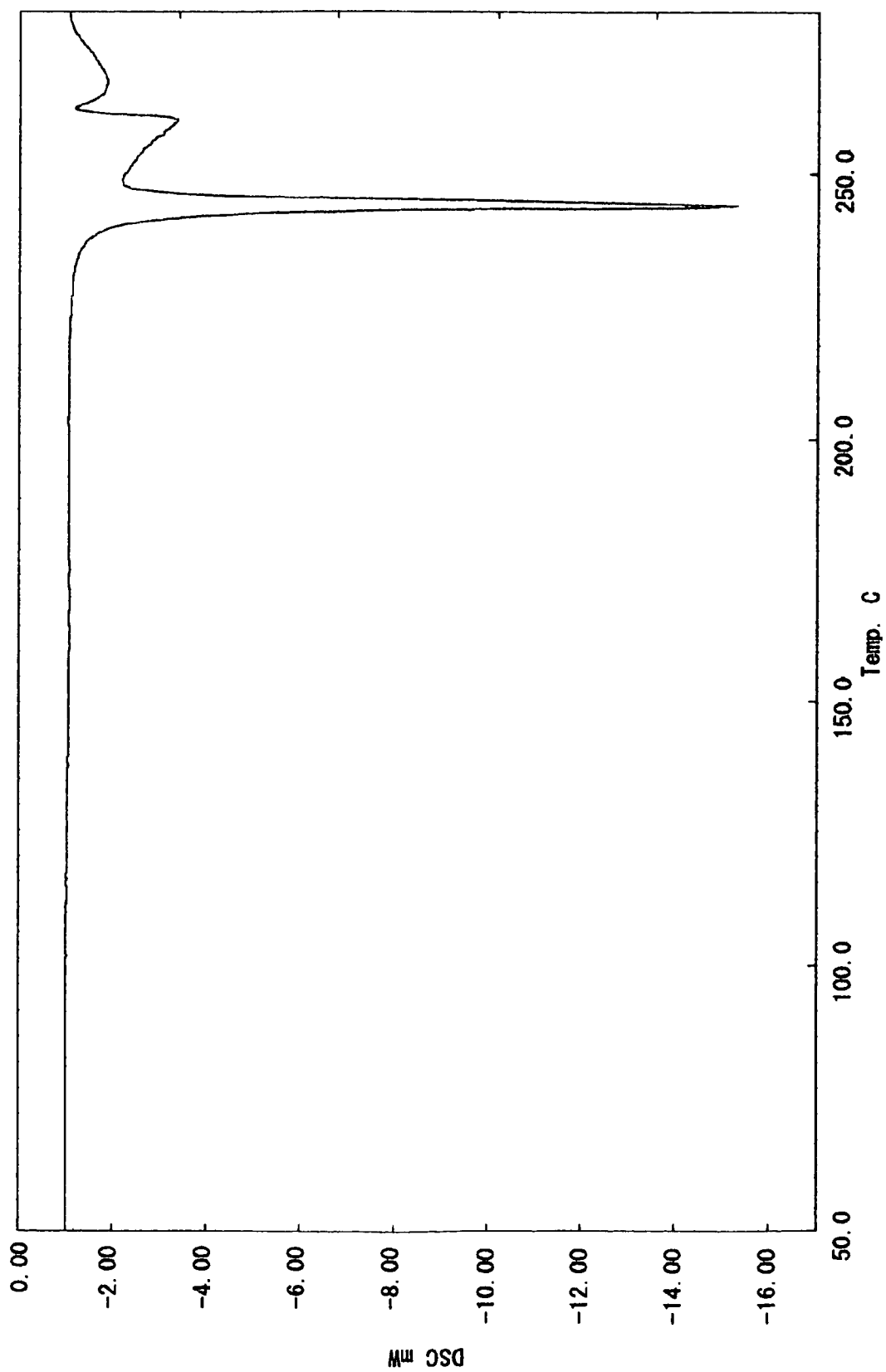
FIG. 2 is a DSC (differential scanning calorimetry) chart of the crystalline compound produced in Example 1.

A DSC chart of the crystalline substance produced in Example 1 is shown in FIG. 2.

In the DSC chart, the crystalline substance according to the present invention produced in Example 1 had one endothermic peak at 244° C. with an onset temperature of 240° C. and a termination temperature of 246° C., indicating that the melting point of the crystalline substance of the present invention produced in Example 1 is in the range of 240 to 246° C. (with decomposition).

Evaluation Example 3

Purity

The purity of the crystalline substance produced in Example 1 was measured by HPLC.

Acetonitrile (10 mL) was added to 0.01 g of the crystalline substance produced in Example 1, and the mixture was then ultrasonicated for dissolution to prepare a sample solution. For 5 µL of this solution, HPLC analysis was performed under the following conditions. After background correction, each peak area was determined by an automatic integration method. Measuring conditions for HPLC were as follows.

Apparatus: 1100 series, manufactured by Agilent

Detector: Ultraviolet absorptiometer (measuring wavelength: 246 nm)

Column: Stainless steel tube (inner diameter 4.6 mm, length 25 cm) packed with 5-µm octadecylsilylated silica gel for liquid chromatography (Mightysil RP-18 GP (4.6×250 mm), manufactured by Kanto Chemical Co., Inc.)

Column temp.: Constant temp. around 40° C.

Mobile phase: Liquid A=5 mmol/L ammonium formate buffer solution (pH 3.8)

Liquid B=methanol

Liquid A and liquid B were fed as shown in the following table.

TABLE 1

| Feed of liquid A and liquid B | | |
|---|---|---|
| | Liquid A (%) | Liquid B (%) |
| 0 min | 45 | 55 |
| 40 min | 45 | 55 |
| 60 min | 0 | 100 |
| 70 min | 0 | 100 |

Flow rate: 1 mL/min

Area measuring range: 3 to 62 min

The crystalline substance produced in Example 1 had a purity of 99% as determined based on percentage area obtained by HPLC analysis.

What is claimed is:

1. Crystalline compound of 2-(1-isopropoxycarbonyloxy-2-methylpropyl)-7,8-dimethoxy-4(5H)10-dioxo-2H-1,2,3-triazolo[4,5-c][1]benzazepine which has diffraction peaks at diffraction angles (2θ): 11.2±0.1°, 14.4±0.1°, 15.5±0.1°, and 25.3±0.1° in a powder X-ray diffraction pattern.

2. The crystalline compound according to claim 1, which has a purity of not less than 99% as determined based on percentage area obtained by HPLC (high-performance liquid chromatography).

3. The crystalline compound according to claim 1 or 2, which has a melting point in the temperature range of 240 to 246° C. (with decomposition) as determined from an endothermic peak in a DSC (differential scanning calorimetry) chart obtained by DSC.

* * * * *